(12) United States Patent
Hawes et al.

(10) Patent No.: US 7,441,336 B2
(45) Date of Patent: Oct. 28, 2008

(54) HAND HELD APPLIANCES

(75) Inventors: Christopher Martin Hawes, Reading (GB); Joseph Roger Yeoman, Kidmore End (GB); David Vince, Melksham (GB)

(73) Assignee: The Gillette Company, Boston, MA (US)

( * ) Notice: Subject to any disclaimer, the term of this patent is extended or adjusted under 35 U.S.C. 154(b) by 61 days.

(21) Appl. No.: 11/202,506

(22) Filed: Aug. 12, 2005

(65) Prior Publication Data

US 2006/0037197 A1   Feb. 23, 2006

(30) Foreign Application Priority Data

Feb. 19, 2002   (GB)   ................... 0303872.6

(51) Int. Cl.
*B26B 19/28* (2006.01)
*B26B 19/12* (2006.01)
*B26B 19/38* (2006.01)

(52) U.S. Cl. .................. 30/45; 30/44; 30/541

(58) Field of Classification Search ............... 30/34.05, 30/42, 44, 45, 50, 537, 541; 15/28
See application file for complete search history.

(56) References Cited

U.S. PATENT DOCUMENTS

| 3,611,568 | A | * | 10/1971 | Alexander et al. | .............. | 30/45 |
|---|---|---|---|---|---|---|
| 3,636,627 | A | * | 1/1972 | Tiffin | .............. | 30/45 |
| 4,380,121 | A |  | 4/1983 | Naimer et al. |  |  |
| 4,531,287 | A |  | 7/1985 | Shibata et al. |  |  |
| 4,744,124 | A |  | 5/1988 | Wang et al. |  |  |
| 4,939,407 | A |  | 7/1990 | Goo et al. |  |  |
| 5,046,249 | A |  | 9/1991 | Kawara et al. |  |  |
| 5,214,851 | A |  | 6/1993 | Althaus |  |  |
| 5,299,354 | A |  | 4/1994 | Metcalf et al. | .............. | 30/45 |
| 5,337,478 | A |  | 8/1994 | Cohen et al. |  |  |
| 5,453,644 | A | * | 9/1995 | Yap et al. | .............. | 307/116 |
| 5,711,328 | A |  | 1/1998 | Gebhard |  |  |
| 6,062,936 | A | * | 5/2000 | Rudell et al. | .............. | 446/71 |
| 6,421,918 | B1 | * | 7/2002 | Dato et al. | .............. | 30/45 |

(Continued)

FOREIGN PATENT DOCUMENTS

DE   3122521   6/1981

(Continued)

*Primary Examiner*—Hwei-Siu C Payer
(74) *Attorney, Agent, or Firm*—Brion A. Berman

(57) ABSTRACT

The invention relates to a hand held electrical appliance having a handle and a head part to be brought into contact with the body of the user, such as a toothbrush with a brush head or a safety razor with a head part in the form of a blade unit, including an electrically operable vibration generating device, for example an electric motor and eccentric weight, and a control device for controlling operation of the vibration generating device. The control device is proximity or touch sensitive and includes a sensor element, such as an electrode formed by a blade of the blade unit, so that the vibration generating device is actuated in response to a person using the appliance and moving the blade unit (or other head part) into close proximity to or into contact with the body area to be treated. Due to the vibration generating device being operated only when the head part is applied or about to be applied to the body, the discomfort of holding a vibrating appliance in the hand, as perceived by a user, is greatly diminished.

24 Claims, 8 Drawing Sheets

U.S. PATENT DOCUMENTS

| | | | |
|---|---|---|---|
| 6,481,104 B1 * | 11/2002 | Parker et al. | 30/45 |
| 6,612,034 B2 * | 9/2003 | Damstra | 30/43.6 |
| 6,792,640 B2 * | 9/2004 | Lev | 15/28 |
| 2002/0088068 A1 | 7/2002 | Levy et al. | |
| 2002/0189102 A1 | 12/2002 | Orloff | |
| 2003/0000032 A1 | 1/2003 | Mordechai | 15/28 |
| 2003/0154832 A1 | 8/2003 | Guimont et al. | |
| 2006/0123631 A1 * | 6/2006 | Szczepanowski et al. | 30/44 |
| 2006/0218804 A1 * | 10/2006 | Noble et al. | 30/440 |

FOREIGN PATENT DOCUMENTS

| | | |
|---|---|---|
| DE | 42 28 859 | 8/1992 |
| DE | 101 17 766 | 10/2002 |
| EP | 0 524 708 | 1/1993 |
| EP | 08 856 98 | 12/1998 |
| EP | 09 068 14 | 7/2001 |
| GB | 2250428 | 6/1992 |
| GB | 2377995 | 1/2003 |
| JP | 05 329024 | 12/1993 |
| JP | 9051740 | 2/1997 |

* cited by examiner

HAND HELD APPLIANCES

CROSS REFERENCE TO RELATED APPLICATIONS

This application claims the benefit of priority under 35 U.S.C. § 120 from WO 2004/1073941 A1, filed on Feb. 19, 2004, which claims priority from GB 080303872.6, filed on Feb. 19, 2003.

TECHNICAL FIELD

This invention relates to hand held appliances, and more especially hand held appliances of a kind having a handle by means of which the appliance is intended to be gripped in the hand of a user, a head part that for the purpose of performing a treatment on the body of the user is brought into contact with, or at least into close proximity to, the body, and an electrical device, such as a vibration generator, operated in use of the appliance.

BACKGROUND

Appliances of the aforementioned kind include safety razors and toothbrushes. Other such appliances could include massaging devices. A toothbrush including a vibration mechanism is described in GB-A-2250428, and in U.S. Pat. No. 4,744,124 there is described a toothbrush including a sound generator which is switched on by pressing the brush head against the teeth. In GB-A-2258922 there is proposed a personal care apparatus such as an electric toothbrush with a capacitive sensor in the handle so that the motor is turned on when the toothbrush is picked up in the hand.

A safety razor generally comprises a handle and a blade unit carried on the handle and including at least one blade with a sharp cutting edge. In the course of shaving, the blade unit is applied against the skin and the blade or blades are moved across the skin so that the sharp cutting edges engage and cut through the hairs protruding from the skin. The blade unit can be fixed on the handle with the intention that the entire razor should be discarded when the cutting edges have become dull and are no longer capable of providing a comfortable shave. Alternatively the blade unit may be removably mounted on the handle so that the blade unit can be replaced by a new blade unit when the sharpness of the blades has diminished to an unacceptable level. Replaceable blade units are often referred to as shaving cartridges.

The majority of safety razors currently marketed are operated and used entirely manually. Nonetheless electrical devices can be incorporated in safety razors and it is known to include an electrically driven vibration mechanism which is operable to vibrate the razor, it having been observed that such vibration can have a beneficial effect on razor performance. A simple and convenient vibration mechanism consists of an electric motor with a weight mounted eccentrically on its output shaft. The vibration mechanism and a battery for providing electric power to the motor can be conveniently housed in the razor handle. Examples of previous proposals for such razors are those described in EP-A-0885698, U.S. Pat. No. 3,611,568, U.S. Pat. No. 5,299,354, U.S. Pat. No. 5,214,851, U.S. Pat. No. 5,046,249 and U.S. Pat. No. 6,481, 104B1. Although vibrating the razor can enhance the razor performance during actual shaving, it is not without drawbacks. Many razor users dislike the feel of a vibrating razor held in the hand and this has led to attempts to design the razor handle so that the vibrations are concentrated at the blade unit and are not transmitted to the part of the handle generally gripped in the hand of a user, as disclosed in U.S. Pat. No. 5,214,851, U.S. Pat. No. 5,046,249 and U.S. Pat. No. 6,481, 104B1.

In EP-A-0906814 there is proposed a safety razor including a piezoelectric element on the razor head for producing a signal dependent on forces exerted on the razor head. It is suggested that a voltage produced in dependence upon the output signal could, inter alia, activate a motor to produce a motion, such as vibration, but the purpose of the vibration is not stated and it could be only to indicate to a user that too much force is being applied or that the blades should be replaced. In any case, since force application can vary during shaving, e.g., when shaving different areas of the face and from user-to-user, switching based on force application has severe limitations.

With the aim of conserving energy and eliminating the need for an on-off switch to control operation of an electric motor in a dry shaver, it has been proposed in U.S. Pat. No. 4,380,121 and U.S. Pat. No. 4,531,287, respectively, to actuate the motor in response to the cutter foil being placed into contact with and into close proximity to, the skin of a person holding the shaver. These dry shavers do not include vibration generators and they do not suggest any solution to the problem of discomfort associated with prior art vibrating safety razors. A hair dryer equipped with an infra red sensor or proximity sensor to control power supply to the fan and heating element is described in DE-A-1967734.

SUMMARY

The present invention is based on the realization that the discomfort perceived from a vibrating razor applies for the most part when the razor is held with the blade unit away from the face, or other body area being shaved, users generally being much happier with the feel of the vibrating razor in the hand when the blade unit is in contact with the body, such as when carrying out a shaving stroke.

In accordance with the invention there is provided a hand held appliance having a handle, a head part for use in performing a treatment on the body of a user of the appliance, an electrically operable vibration generating device, and a control device to control operation of the vibration generation device, wherein the switching device is proximity or touch sensitive and includes a sensor element located at the head part whereby the vibration generating device is actuated in response to a user of the appliance moving the head part into close proximity to or into contact with the body for treating the body.

The invention can be embodied in different forms of hand held appliance. Thus, the appliance can be a toothbrush, in which case the sensor will be located at the brush head and may control, through the control device, a mechanism for vibrating the brush level. The control device can also control one or more further devices, such as a pump motor or valve actuator for delivering a toothpaste or other substance to the brush head, or a mechanism for oscillating the brush head. The principles underlying the invention are applicable to hand held appliances of the kind initially mentioned above, but the invention is particularly described herein below with reference to safety razors.

The invention is applicable to a safety razor with a head part in the form of a blade unit. In the case of a wet razor equipped with a proximity sensitive control device, the device should be activated when the blade unit is within a distance of not more than about 10 mm from the body, such as a distance of 5 mm or less. Proximity switches operated by light, infrared, or radio frequency radiation may be used. In one embodiment of a safety razor, a touch sensitive control device is employed whereby actuation occurs immediately upon the blade unit making contact with the skin. By the present invention the drawback of prior art vibrating safety razors as explained above is precluded by the vibration generating device being activated only when the blade unit is contacting or about to be brought into contact with the skin. However, it is not essential for the control device to act as an on/off switch and it could instead be arranged, for example, to change the frequency of vibration when the blade unit is presented against the skin to be shaved. A small amount of low frequency vibration when the blade unit is held away from the skin, such as when a user first picks up the razor, may be desirable to provide a tactile indication that the razor is ready for use. The frequency of vibration during actual shaving is not critical and vibration at ultrasonic frequencies as well as subsonic frequencies is possible within the scope of the invention.

The vibration mechanism may be adapted to vibrate only one or more selected components of the blade unit, such as the guard which contacts the skin in front of the blades, or one or more blades, and the vibration may be directional, for instance directed lengthwise of the blades to encourage a slicing cutting action or transverse to the blades. Another possibility is an element vibrated in a direction generally perpendicular to the skin surface being shaved. The vibration mechanism may incorporate a piezoelectric device for producing the vibrations. Alternatively a motor for rotationally driving an eccentric weight can be controlled by the control device. The sensor element located on the blade unit is preferably an electrode and can conveniently be constituted by at least one blade of the blade unit. A separate electrode can however, be provided instead if preferred. The blade unit may include a plastic frame at least part of which may be made of conductive plastics to provide an electrode and/or to provide electrical connection to the electrode. Electrical connection to the electrode can also be achieved by plating or coating the blade unit frame with an electrically conductive material or equipping the blade unit with one or more conductive strips for this purpose.

In certain embodiments a second electrode is provided and the control device is sensitive to a change in an electrical parameter, such as the electrical resistance or capacitance between the electrodes. More particularly the second electrode is arranged so as to be, in use, in close proximity to or in contact with the body of the user, and is conveniently provided as part of the handle for contact with the hand of a user holding the razor or other appliance according to the invention.

The control device may include a signal generator arranged to generate a pair of electrical signals, a comparator arranged to compare the pair of electrical signals and to provide an output indicative of a predetermined change in the relationship between the pair of signals, and output means responsive to the comparator output to actuate the electrical device, the predetermined change occurring when both electrodes are in close proximity to or in contact with the body of the appliance user.

In particular embodiments, the signal generator is an oscillator, the pair of electrical signals is a pair of oscillating signals, and first and second capacitances are arranged to be charged by the respective oscillating signals, the electrodes being arranged such that the first capacitance is charged more slowly than the second capacitance when the appliance is moved by a user into a condition where both electrodes are in close proximity to or in contact with the body, e.g., due to a further capacitance being coupled in parallel with the first capacitance.

The hand held appliances described herein can include an electric power source, for example, a battery, to supply electric power for the control means and the vibration generating device, as well as a switch device arranged to connect or interrupt the supply of electric power from the electric power source to the control device and vibration generating device. The switch device may be on the exterior of the appliance and manually operable by the user. Alternatively, it may be arranged to interact with an associated storage tray to interrupt the supply of electric power from the electric power source when inserted into the storage tray and to connect the supply when removed therefrom. The storage tray can be generally of the same form as that described in U.S. Pat. No. 5,782,346, which is incorporated herein by reference in its entirety.

Other forms of electrical devices in addition to a vibration generating device as described above may be included in a safety razor embodying the invention.

Examples of such devices include: (i) heating devices for heating one or more blades or other components of a blade unit that contact the skin during shaving, such as Peltier devices or electrical resistance or ohmic heating devices; (ii) dispensing devices for delivering a shaving enhancement product to the skin and that may be activated by operation of a motor driven pump or by operation of a valve having an electrically controlled actuator, shaving enhancement products that can be delivered at a safety razor blade unit during performance of a shaving stroke including those with the qualities and properties mentioned in our U.S. Pat. No. 6,789, 321, the contents of which are incorporated herein by reference in their entirety; and (iii) a conditioning device to prepare the skin and/or hairs ready to be cut by the blades, such as a roller mounted in the region of the guard of the blade unit and adapted to be rotated about its axis for encouraging hairs lying against the skin to stand up for cutting.

All of these forms of electrical devices can be controlled by the control device including a sensor element located at the blade unit is described herein. It is possible also for the sensor and control device to operate a counter which can give an indication of the number of times the blade unit is applied against the skin and thereby signal when replacement of the blade unit is due.

DESCRIPTION OF DRAWINGS

To facilitate a clear understanding of the invention, an embodiment of a safety razor is described in detail below with reference to the accompanying drawings, in which.

DETAILED DESCRIPTION

Figure 1:
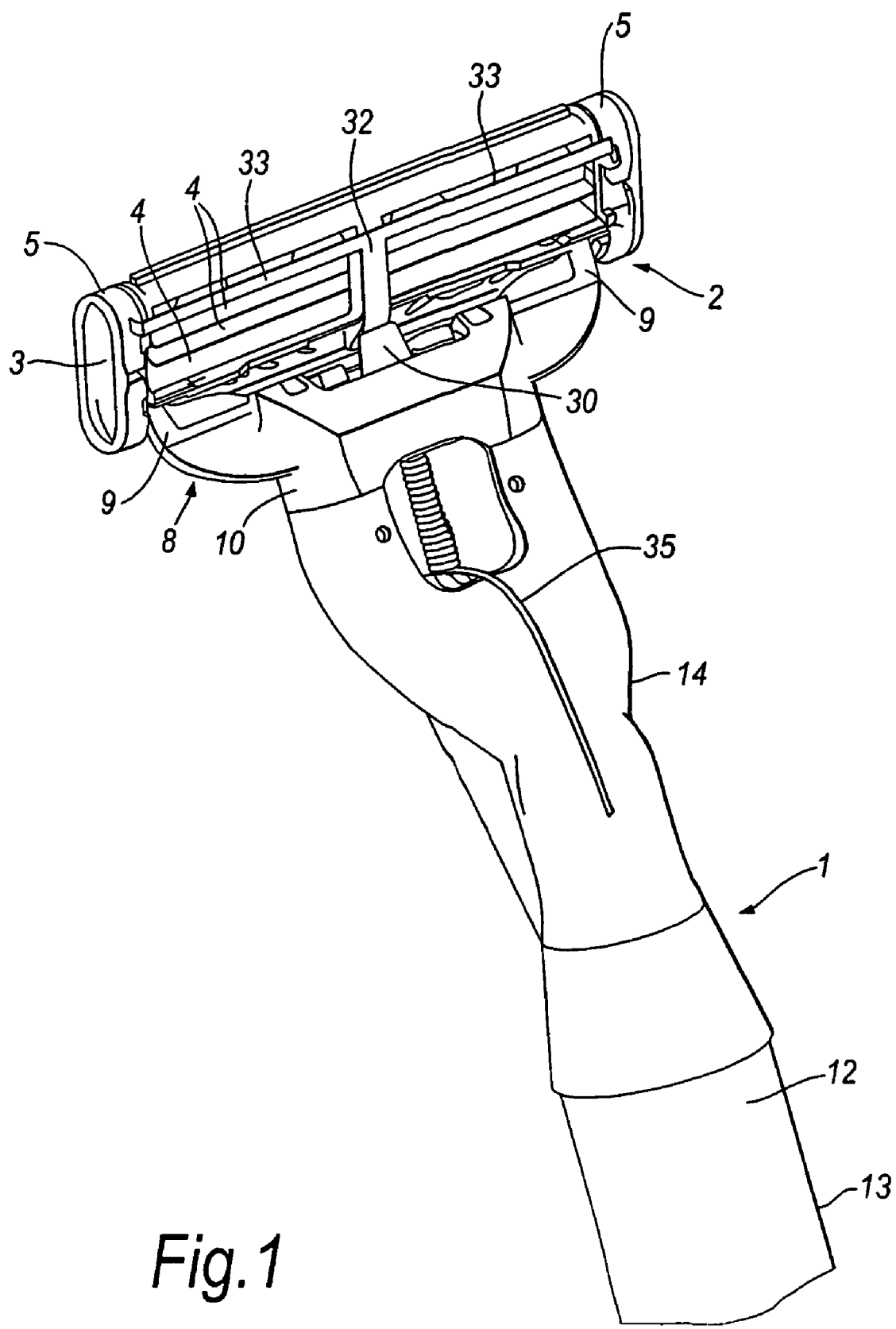
FIG. 1 is a partial isometric view of the razor illustrating the blade unit and an upper portion of the handle as seen from the rear.

The safety razor illustrated in the drawings has a handle 1 and a blade unit or cartridge 2 detachably mounted on the upper end of the handle. The blade unit includes a generally rectangular frame 3, and a plurality of blades 4, e.g., 3, 4 or 5 blades, with substantially parallel sharp cutting edges, disposed in the frame and held in place by metal clips 5 positioned around the frame 3 at the opposite ends of the blade unit 2. A guard structure including a strip of elastonieric material is provided on the frame for contacting the skin in front of the blades, and a cap structnrc including a lubricating strip is provided on the frame for contacting the skin behind the blades during the performance of a shaving stroke. The frame is pivotaily carried on yoke member 8 having a pair of arms 9 which extend from a hub 10 and are journalled in opposite ends of the frame 2 so that the blade unit 2 can pivot relative to the handle 1 about an axis substantially parallel to the blade edges. The hub 10 is connected detachably to the end of the handle 1. As so far described the razor is of a known construction and for further details reference may be made to earlier patent publications, one example of which is U.S. Pat No. 5,787,586, the contents of which is incorporated herein by references in its entirety.

The razor handle includes a main portion 12 intended to be gripped in the hand and a neck 14 extending upwardly from the main portion and to the free end of which the blade unit 2 is attached. The main or gripping portion 12 of the handle 1 includes an electrically conductive, e.g., metal casing 13 which serves as an electrode for electrical contact with the hand of a user as described in more detail below. Housed within a battery compartment in the handle is a replaceable or rechargeable battery 15. Also housed within the handle is electronic control device 16. The battery 15 is electrically connected to the control device 16 through a power switch which is operable to interrupt power supply to the control device for conserving battery energy during periods when the razor is not being used. The power switch could be located on the handle for manual operation, but in a preferred construction the power switch is arranged to be actuated by removing the razor from, and returning it to, a razor holder on which the razor is intended to be stored when not in use.

Figure 2:
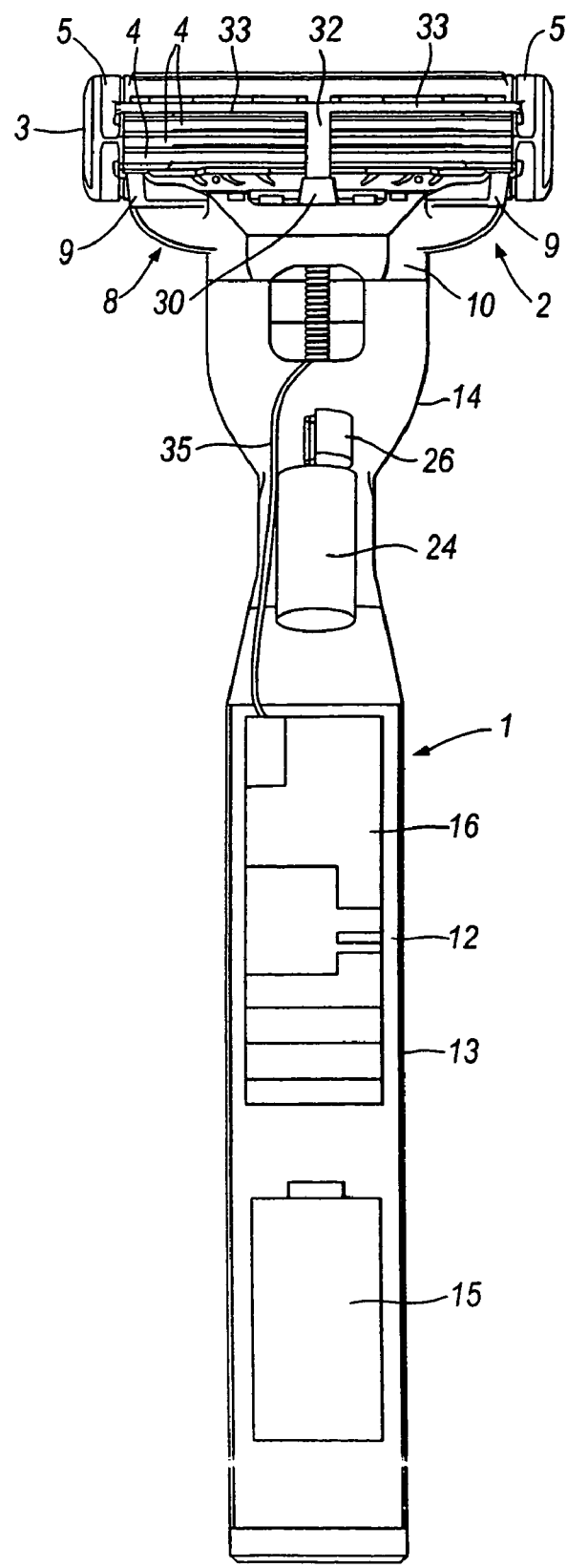
FIG. 2 shows the razor in rear elevation.
Figure 3:
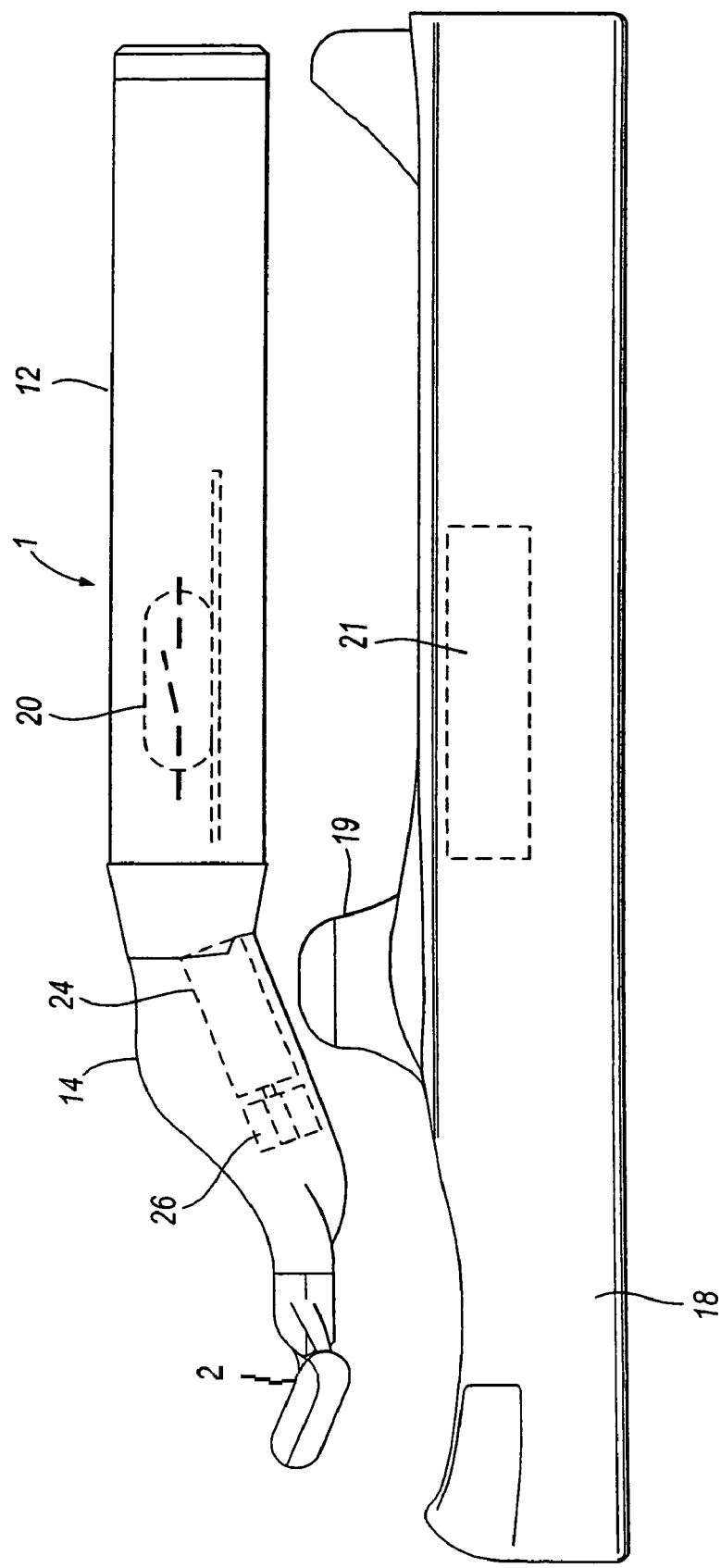
FIG. 3 is a side elevation showing a razor holder in the form of a tray on which the razor is stored during periods of non-use, the razor being shown separated from the storage tray at a small distance.
Figure 4:
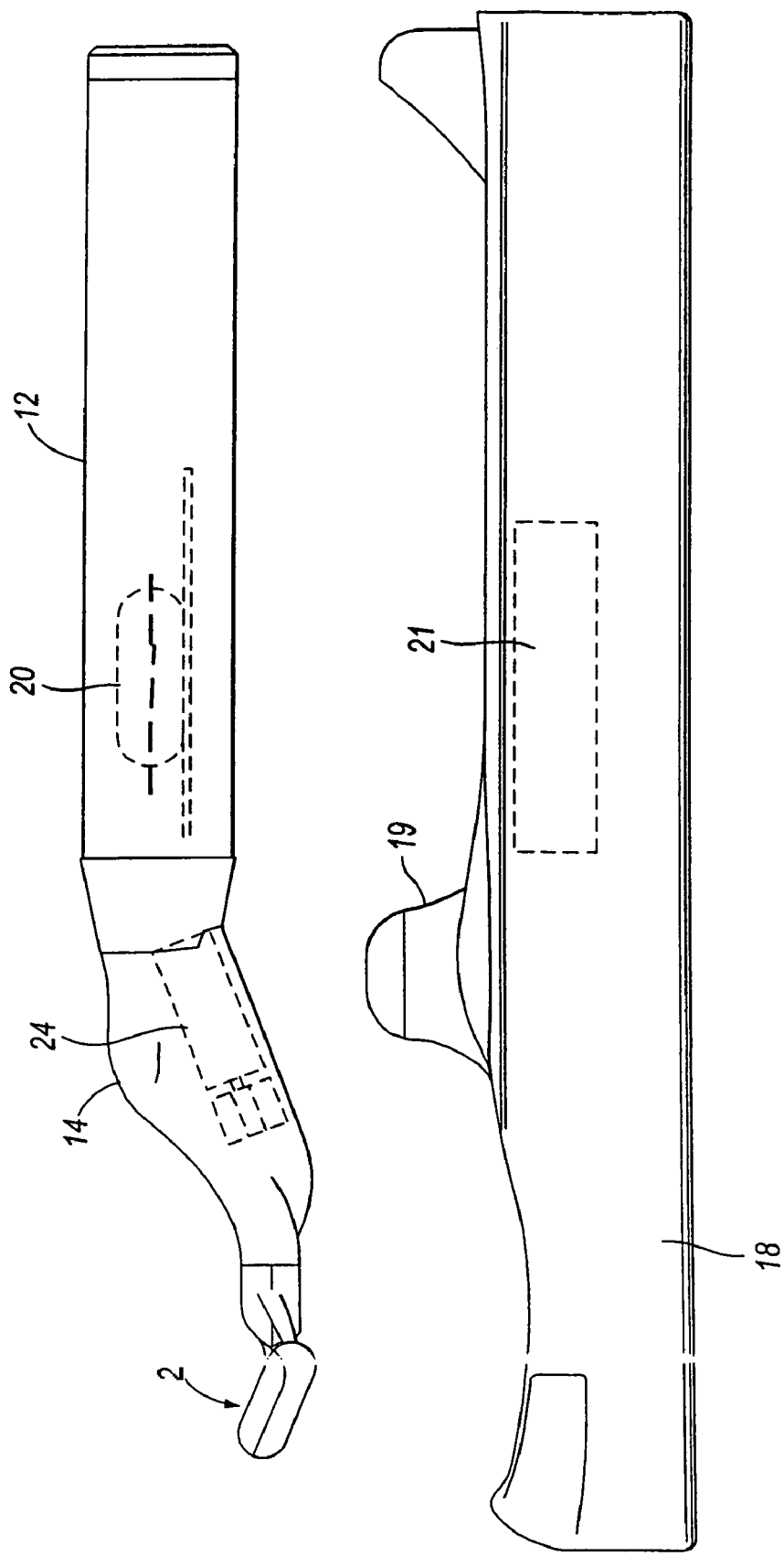
FIG. 4 is a side elevation corresponding to claim 3, but showing the razor at a greater distance form the storage tray.
Figure 5:
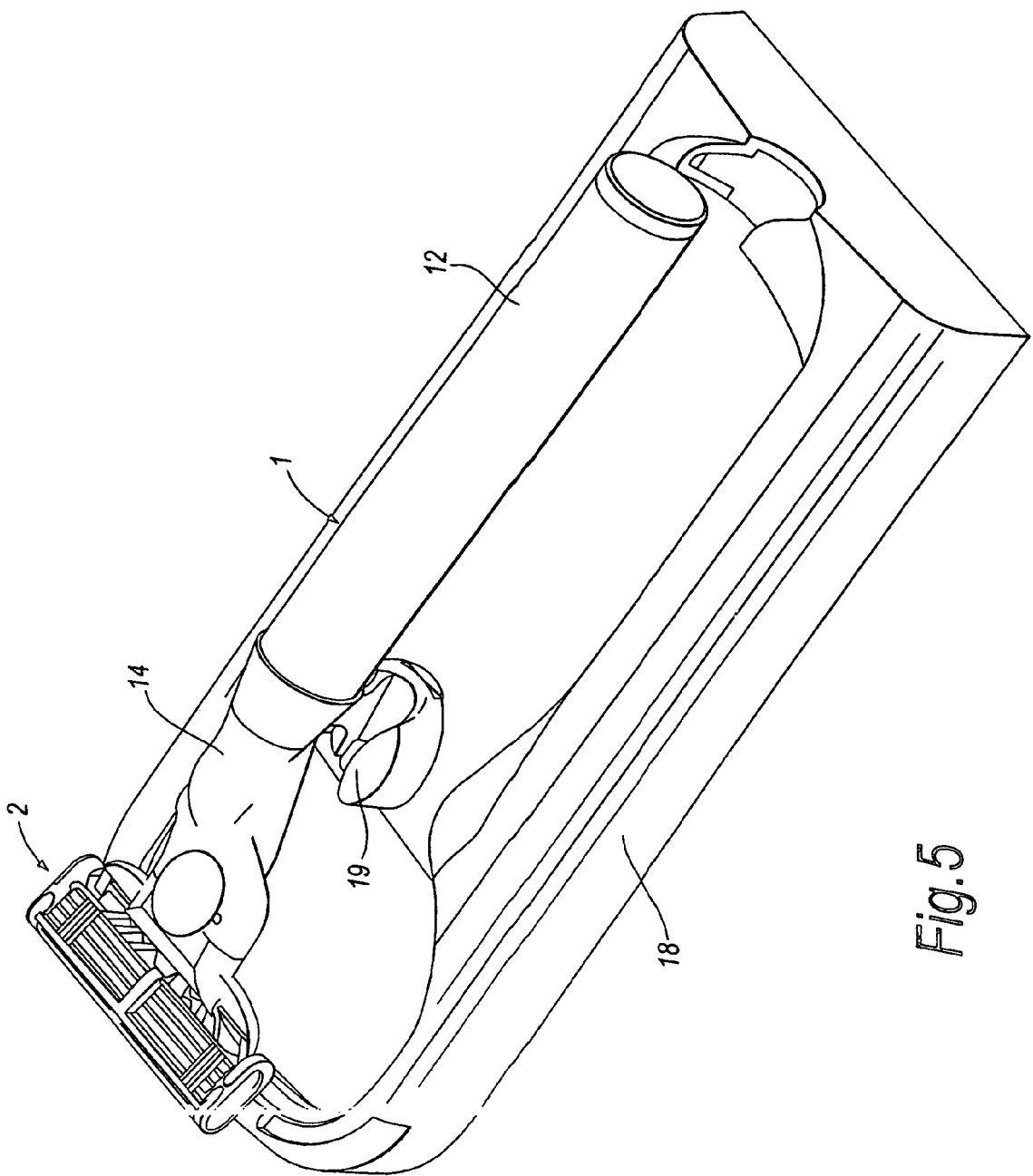
FIG. 5 shows the razor and storage tray of FIG. 3 in an isometric view.
Figure 6:
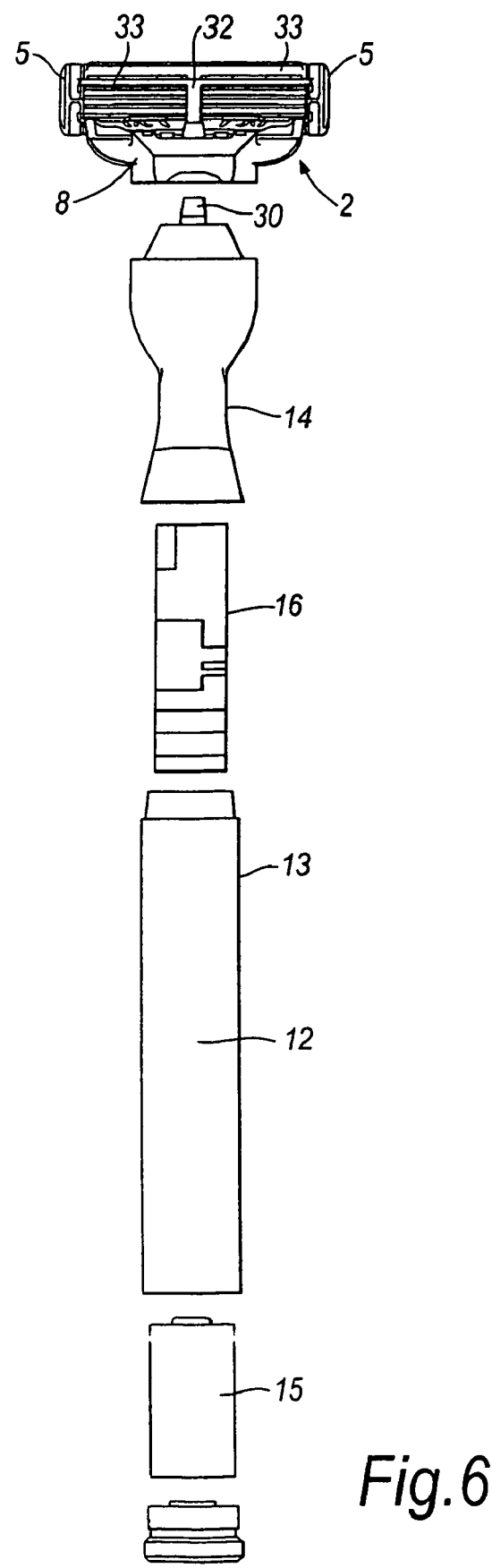
FIG. 6 is an exploded rear elevation of the razor.

A known form of razor holder consists of a tray 18 as shown in FIGS. 3-5, the tray 18 having on its upper side a saddle 19 adapted to receive and lightly grip the neck 14 of the razor handle 1. The razor handle 1 could be equipped with a mechanical switch so arranged for cooperation with the storage tray 18 that the switch is operated automatically when the razor is lifted away from the storage tray 18 for power to be supplied to the switching device 16 from the battery 15, and to be actuated upon replacement of the razor on the tray to interrupt the power supply. In one embodiment, essentially the same result is achieved by a power switch in the form of a reed switch 20 located within the handle 1, the storage tray 18 being provided with a permanent magnet 21. When the razor is positioned close to the tray 18 the reed switch 20 is held open by the proximity of magnet 21 and there is no electrical power supply from the battery 15, as shown in FIG. 3, but when the razor is moved away from the tray the reed switch 20 closes and electrical power supply to the control device 16 is established. The control device 16, in a manner described in detail below, controls actuation of an electric motor 24 (FIGS. 2 and 3) housed within the handle 1 and having an output shaft with an eccentric weight 26 fastened thereon. In a manner known per se, energization of the electric motor results in a high speed rotation of the eccentric weight 26 and thereby vibration of the razor, and the blade unit 2 in particular, for enhancing the shaving performance of the razor. A suitable vibration frequency is about 120 Hz.

The control device 16 is configured, in one embodiment, to be touch sensitive so that the motor 24 is actuated only when the blade unit of the razor is in contact with the body of the razor user, that is a person holding the razor handle 1. The blade unit 2 incorporates an electrode which is conveniently constituted by at least one and preferably includes all of the blades 4 of the blade unit. Electrical connection between the control device 16 and this electrode 4 is achieved by the neck 14 of the handle 1 having a contact 30 arranged to project through the hub 10 of the yoke member 8 and to bear against a contact strip 32 fixed to the rear of the blade unit, the contact strip 32 having lateral wings 33 which extend to and are conductively connected to the metal blade retention clips 5, and these clips in turn having contact with blades 4. Of course, it is not essential to use the blades 4 as an electrode and a separate electrically conductive element could be provided on the blade unit in a position for contacting the skin when the blade unit 2 performs a shaving stroke. The contact 30 makes constant electrical contact with the contact strip 32 so that the electrical continuity between the electrode at the blade unit is not interrupted even during pivoting of the blade unit 2 on the handle 1 as tends to occur as the blade unit is applied to and moved across the skin. The contact 30 conveniently takes the form of a spring-loaded plunger for resisting pivotal movement of the blade unit away from a predetermined rest position. The contact 30 is shown connected electrically to the control device 16 by a wire conductor 35 which is led through the neck 14 of the handle 1.

Of course, there are other possibilities to ensure electrical connection of the electrode on the blade unit and the control device. For example, the frame 3 of the blade unit could be made of an electrically conductive material, such as a conductive plastics. Also the rear of the frame 3 could be plated, coated, or printed with conductive material, have an adhesive metal foil applied to it, or have a metal element embedded therein, to provide electrical connection between the contact 30 and the clips 5, or to the electrode itself or another component in contact with the electrode. Alternatively the frame may include an injection molded metal part to provide the conductive path between the electrode and the contact 30, or water held in capillary grooves may be sufficient to ensure the electrical continuity.

Figure 7:
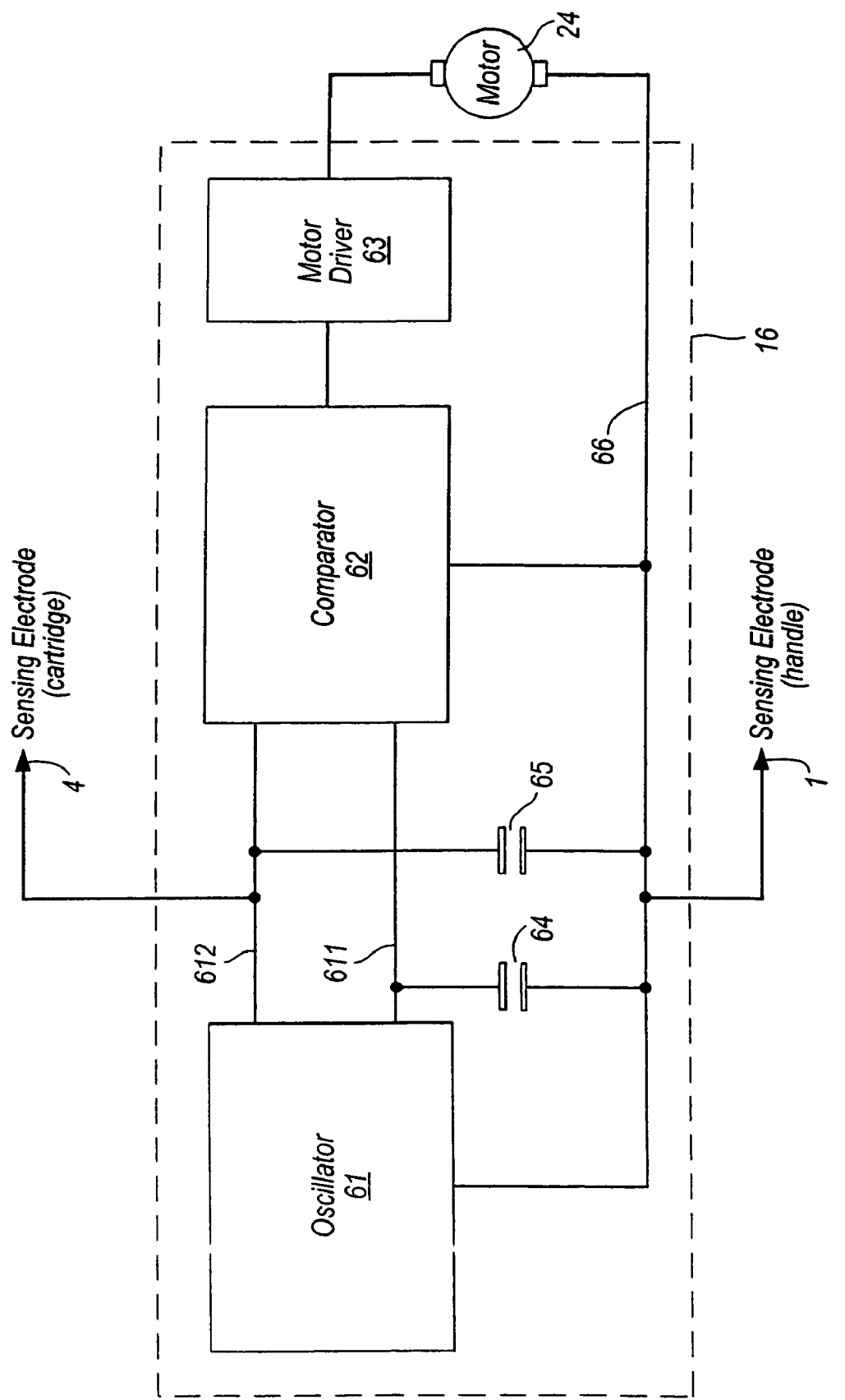
FIG. 7 is a block diagram of an electric switching device incorporated in the razor.

FIG. 7 is a schematic diagram to illustrate the function of control device 16. As shown, control device 16 comprises an oscillator 61, a comparator 62, motor driving circuitry 63 and first and second capacitors 64, 65. Control device 16 is additionally connected to two sensing electrodes constituted by the blades 4 as described above and the exterior casing 13 of the handle 1 respectively. Motor driving circuitry 63 is connected to provide the drive current to motor 24. As mentioned above, the power necessary to energize control device 16 is provided by battery 15 through a power switch. The power connections are omitted from FIG. 7 for clarity, it being understood that the following description of the operation of control device 16 is applicable to the condition when it is energised by the application of power from the battery.

Oscillator 61 is configured to provide two oscillating signals on output lines 611 and 612 respectively. Output lines 611 and 612 are connected to line 66, which serves as a ground line for the circuitry, via first and second capacitors 64, 65 respectively. Lines 611 and 612 further provide a pair of inputs to comparator 62. In essence, the comparator 62 is sensitive to changes in the relationship between its two inputs. The sensor electrodes are connected such that the relationship between the two inputs to the comparator changes according to whether both or only one of the electrodes are in contact with the body of a user. Being sensitive to such a change, the comparator switches the motor driver circuitry 63 on when both electrodes are in contact with the body of a user.

In more detail, it will be seen in FIG. 7 that line 612 is additionally connected to one of the sensing electrodes. When there is no effective electrical connection between the two electrodes, the signals output by oscillator 61 on lines 611 and 612 have a first predetermined relationship at the input to comparator 62.

When both of the sensing electrodes are in contact with the body of a user some additional electrical connection is made between line 612 and ground line 66. This may be for instance capacitance additional to capacitor 65 and/or for electrical resistance. In any event, the additional connection is effective to alter the characteristics of the signal on line 612 input to comparator 62. Accordingly the relationship between the two inputs changes and the comparator 62 responds by activating motor driving circuitry 63 and so activating motor 24.

As described above, control device 16 is responsive to both of the sensing electrodes being in contact with the body of the user. Depending upon the operating conditions of the device or the sensitivity of the comparator control device 16 may also be responsive to other conditions. In particular, if a user is holding the shaving device and is therefore in contact with one of the electrodes, it may be sufficient to bring the other electrode close to but not touching his or her body. The proximity of the other electrode to the body is sufficient in this case for an additional capacitance to appear between lines 612 and 66 and so cause the above described change in the signals on line 612. The sensitivity of the comparator or other circuit proximity can be set to determine the approximate distance from the body at which this effect will occur. This may for instance be set to be approximately 10 mm.

Further it is the case that other factors may be arranged to cause the electrical characteristics of the circuit to alter sufficiently to trigger the device. For instance, in certain conditions it is found that when a user holding the device and therefore in contact with one of the electrodes rinses the head of the device under running water and therefore brings the other electrode into contact with the water this causes sufficient change in the electrical conditions between the electrodes to trigger the device. In some circumstances, such operation is advantageous.

In various embodiments within this invention, variations on the arrangement of FIG. 7 are possible. As mentioned above, the invention may be configured to activate some device other than the motor 24 as well as or instead of the motor. In such a case motor driving circuitry would be replaced or supplemented by circuitry suitable for providing the current required by such other device.

Further, control means 16 may be arranged to provide some form of output whenever it is energized by the power switch 20 connecting the battery power to the control means. Control means 16 may be provided with a secondary input to the motor driving circuitry 63 such that the motor is driven to provide a low level vibration immediately the control means is energised which alters to a greater level of vibration upon sensing as described above. A lighting device may be provided as part of the hand held device arranged to be lit whenever the power switch is "on." This or a further lighting device may be arranged to flash when battery power is low.

Figure 8:
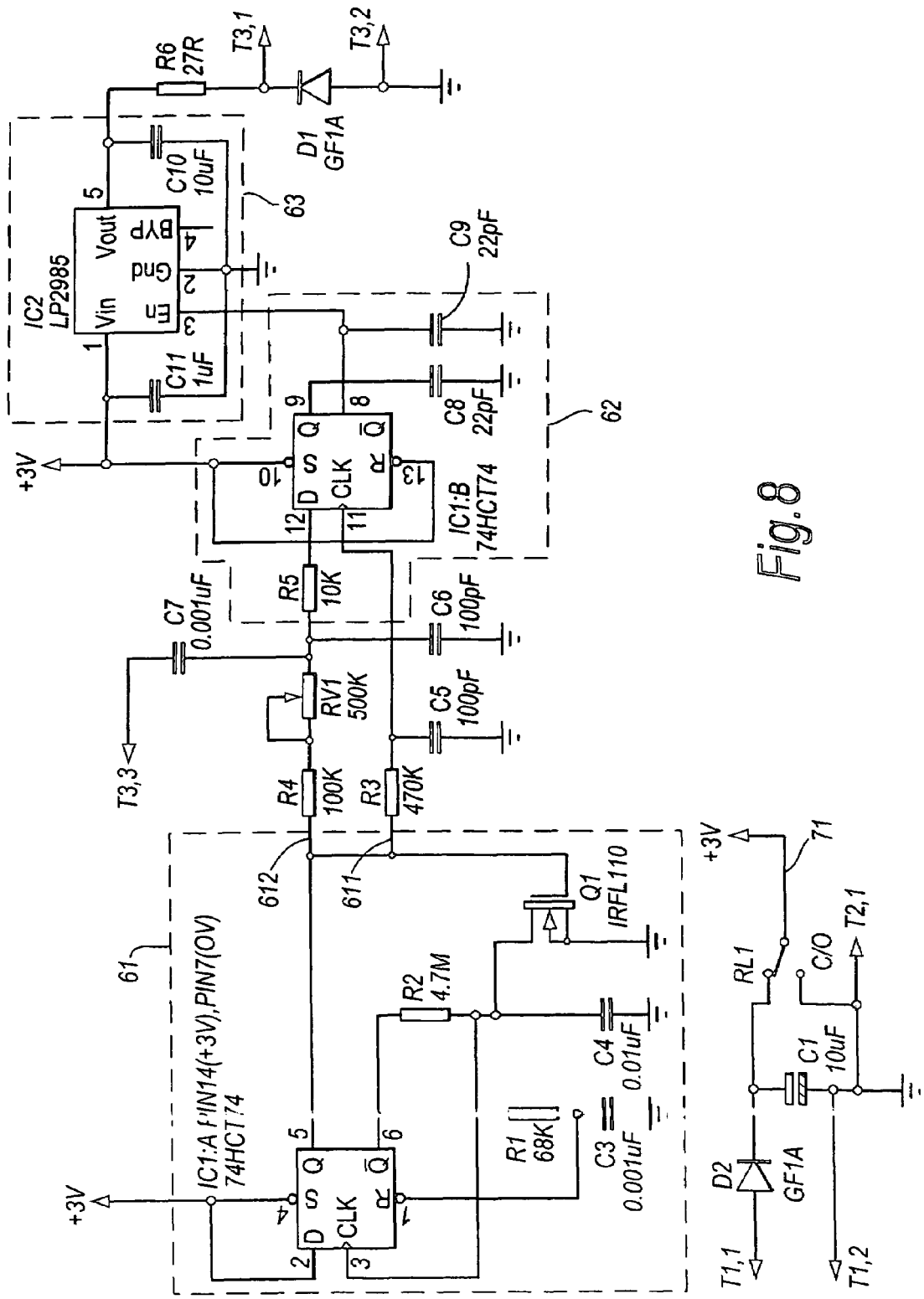
FIG. 8 shows an example of a specific embodiment of a switching circuit.

FIG. 8 illustrates a circuit implementation of the control device 16 of FIG. 7. This is shown merely by way of illustration and many other ways of implementing the functionality of the control device 16 are possible. In FIG. 8, IC1:A, IC1:B and IC1:C are integrated circuit devices and other components are resistors, capacitors, diodes and transistors designated by the prefixes R, C, D and Q with exemplary values being shown in the Figure.

In FIG. 8, RL1 is the power switch described earlier and is a reed switch operated by a magnet in the tray designed to hold the device when not in use. When the device is removed from the tray, the switch RL1 is in the position illustrated such that the power from battery 15 connected to terminals T1,1 and T1,2 is applied to the circuit via the +3V rail, 71. Terminal T2,1 is connected to the exterior casing 13 of the handle 1 of the device to provide one of the two electrodes and the "ground" for the circuit.

IC1:A forms the heart of the oscillator 61 and is configured with associated resistors R1, R2, capacitors C3, C4 and transistor Q1 to provide an oscillation output on lines 611 and 612. These provide the inputs to comparator 62, at the heart of which IC1:B, via resistor and capacitor networks R4, RV1, and C6, and R3 and C5.

Within each cycle of the oscillating signal, when the signal on line 611 goes high, capacitor C5 starts to charge via resistor R3. Therefore, a rising signal is applied to the clock input of IC1:B. At a certain level of this input signal, the clock input of IC1:B changes from low to high. The frequency of the oscillation and the charging rate of capacitor C5 are set such that the "high" clock input to IC1:B is reached during each oscillator cycle. As is well known whenever the clock signal goes high, the value of the "D" input to IC1:B is clocked through to the Q output, with Q being the inverse.

Also within each cycle of the oscillating signal, when the signal on line 612 goes high, capacitor C6 starts to charge via resistor R4 and variable resistor RV1. As capacitor C6 has the same value as capacitor C5, when nothing is connected to terminal T3,3 and RV1 is set so that the combination of R4 and RV1 is equivalent to R3, the charging rate of the two capacitors is the same. Therefore RV1 can be used to trim the circuit to ensure that, in this condition, C6 charges at least as quickly as C5 such that when the clock input to IC1:B goes high, the 'D' input from line 612 is also high. In this condition Q is always low and the motor driving circuitry 63 is not enabled.

Terminal T3,3 is connected to the electrode in the head of the hand held device. Accordingly, when that electrode is brought into contact with or close proximity to the body of a user who is holding the handle connected to terminal T2,1, an additional path to ground is made, via a capacitor C7 and whatever resistance and capacitance the user's body has. This has the effect of slowing the charging rate of capacitor C6 such that, when the clock input of IC1:B goes high, the 'D' input is still low and so Q goes high.

Motor 24 is connected to terminals T3,1 and T3,2 and is driven by standard motor driven circuit IC2. This circuit is enabled by the value of Q of IC1:B going high, thereby activating the motor 24 when the head of the device is placed against the user's skin.

As described above, the control device functions so that the motor 24 stops immediately when the blade unit of the razor is moved out of contact with the skin. This is not essential and the control device can be arranged to provide a short delay of up to a few seconds, e.g., around 0.1-0.5 seconds, before turning off the power supply to the motor after contact between the blade unit and the skin of the user is interrupted, which may be beneficial in maintaining the vibration of the razor between shaving strokes performed in quick succession.

It should be understood that the foregoing description is given by way of non-limiting example only and that modifications are possible without departing from the scope of the invention as defined by the claims which follow. As an example of one possible modification it is mentioned that the conductive casing 13 of the handle could be provided with a thin covering layer of insulating material so that there is a high capacitance and high resistance coupling between the hand of the user and the handle electrode. Furthermore, if desired a manually operable switch mechanism can be included on the razor handle and be connected electrically in series with the switch 20, for use by a user who prefers not to use the storage tray 18 for holding the razor when it is not being used. This switch, or a different switch, such as an electronic toggle switch which turns on and/or off after a certain delay may be included in order to allow the razor user to select a non-vibrating mode, for example when trimming hair in awkward areas.

OTHER EMBODIMENTS

A number of embodiments of the invention have been described. Nevertheless, it will be understood that various modifications may be made without departing from the spirit and scope of the invention.

What is claimed is:

1. A hand held appliance comprising
    a handle;
    a safety razor blade unit configured to be detachably connected to said handle, said unit comprising a guard surface, a cap surface, and a plurality of blades comprising elongated sharp cutting edges, wherein the blades are disposed between the guard and cap surfaces;
    an electrically operable vibration generating device operable to vibrate the blade unit; and
    a control device to control operation of the vibration generating device, wherein the control device is in proximity or is touch sensitive and comprises a sensor element located at the blade unit, the sensor element comprises two electrodes,
    whereby the vibration generating device is actuated in response to a user of the appliance moving the blades into close proximity to, or into contact with, the user's body for cutting hair,
    wherein the control device is sensitive to a change in an electrical parameter between the electrodes,
    wherein said control device comprises a signal generator arranged to generate a pair of electrical signals, and a comparator arranged to compare said pair of electrical signals and to provide an output indicative of a predetermined change in the relationship between said pair of signals, there being an output produced to actuate said vibration generating device; wherein said electrodes are arranged such that movement of the appliance by the user into a condition where both electrodes are in close proximity to or in contact with the body causes said predetermined change.

2. A hand held appliance of claim 1, wherein said signal generator is an oscillator and said pair of electrical signals is a pair of oscillating signals.

3. A hand held appliance of claim 2, wherein said control device comprises first and second capacitances respectively arranged to be charged by said pair of oscillating signals, said electrodes being arranged such that the first capacitance is charged more slowly than the second capacitance when the appliance is moved by a the user into a condition where both electrodes are in close proximity to or in contact with the body.

4. A hand held appliance of claim 3, wherein said electrodes are arranged to couple a further capacitance in parallel with said first capacitance when the appliance is moved by the user into a condition where both electrodes are in close proximity to or in contact with the body.

5. A hand held appliance comprising
    a handle;
    a safety razor blade unit configured to be detachably connected to said handle, said unit comprising a guard surface, a cap surface, and a plurality of blades comprising elongated sharp cutting edges, wherein the blades are disposed between the guard and cap surfaces;
    an electrically operable vibration generating device operable to vibrate the blade unit;
    a control device to control operation of the vibration generating device, wherein the control device is in proximity or is touch sensitive and comprises a sensor element located at the blade unit, whereby the vibration generating device is actuated in response to a user of the appliance moving the blades into close proximity to, or into contact with, the user's body for cutting hair;
    an electric power source arranged to supply electric power for said control device and said vibration generating device; and
    a switch device arranged to connect or interrupt the supply of electric power from said electric power source to said control device and said vibration generating device, wherein said switch device is arranged to interact with an associated storage tray to interrupt the supply of electric power from said electric power source when the appliance is inserted into the storage tray and to connect the supply when the appliance is removed therefrom.

6. A hand held appliance of claim 5, wherein said switch device is a reed switch a arranged to interact with a magnet provided in said storage tray.

7. A hand held appliance comprising
    a handle;
    a head part for use in performing a treatment on a body of a user of the appliance; an electrically operable vibration generating device;
    a control device to control operation of the vibration generating device, wherein the control device is in proximity or touch sensitive and comprises a sensor element located at the head part, whereby the vibration generating device is actuated in response to a user of the appliance moving the head part into close proximity to, or into contact with, the body for treating the body;
    an electric power source arranged to supply electric power for said control device and said vibration generating device; and
    a switch device arranged to connect or interrupt the supply of electric power from said electric power source to said control device and said vibration generating device, wherein said switch device is arranged to interact with an associated storage tray to interrupt the supply of electric power from said electric power source when the appliance is inserted into the storage tray and to connect the supply when the appliance is removed therefrom.

8. A hand held appliance of claim 7, wherein the appliance is a safety razor with a head part in the form of a blade unit, and wherein the vibration generating device is operable to vibrate at least a component of the blade unit.

9. A hand held appliance of claim 8, wherein the vibration generating device comprises an electric motor controlled by the control device.

10. A hand held appliance of claim 9, wherein the vibration generating device comprises a rotatable eccentric weight arranged to be rotated by the electric motor.

11. A hand held appliance of claim 8, wherein the control device is arranged to provide a delay of up to a few seconds in deactivating the vibration generating device in response to the blade unit being moved away from contact with the body of the user.

12. A hand held appliance of claim 11, wherein the control device is arranged to provide a delay of 0.1 to 0.5 seconds.

13. A hand held appliance of claim 8, wherein the sensor element comprises an electrode comprising a blade of the blade unit.

14. A hand held appliance of claim 7, wherein the sensor element comprises an electrode.

15. A hand held appliance of claim 14, further comprising a second electrode and wherein the control device is sensitive to a change in an electrical parameter between the electrodes.

16. A hand held appliance of claim 15, wherein the second electrode is arranged so as to be, in use, in close proximity to or in contact with the body of the user.

17. A hand held appliance of claim 15, wherein said second electrode is provided as part of the handle.

18. A hand held appliance of claim 15, wherein the electrical parameter is electrical resistance.

19. A hand held appliance of claim 15, wherein the electrical parameter is electrical capacitance.

20. A hand held appliance of claim 15, wherein said control device comprises a signal generator arranged to generate a pair of electrical signals, and a comparator arranged to compare said pair of electrical signals and to provide an output indicative of a predetermined change in the relationship between said pair of signals, there being an output produced to actuate said vibration generating device; wherein said electrodes are arranged such that movement of the appliance by a the user into a condition where both electrodes are in close proximity to or in contact with the body causes said predetermined change.

21. A hand held appliance of claim 20, wherein said signal generator is an oscillator and said pair of electrical signals is a pair of oscillating signals.

22. A hand held appliance of claim 21, wherein said control device comprises first and second capacitances respectively arranged to be charged by said pair of oscillating signals, said electrodes being arranged such that the first capacitance is charged more slowly than the second capacitance when the appliance is moved by the user into a condition where both electrodes are in close proximity to or in contact with the body.

23. A hand held appliance of claim 22, wherein said first and second electrodes are arranged to couple a further capacitance in parallel with said first capacitance when the appliance is moved by the user into a condition where both electrodes are in close proximity to or in contact with the body.

24. A hand held appliance of claim 7, wherein said switch device is a reed switch arranged to interact with a magnet provided in said storage tray.

* * * * *